United States Patent
Kaib et al.

(10) Patent No.: US 11,992,693 B2
(45) Date of Patent: *May 28, 2024

(54) SYSTEMS AND METHODS FOR DETECTING HEALTH DISORDERS

(71) Applicant: ZOLL Medical Corporation, Chelmsford, MA (US)

(72) Inventors: Thomas E Kaib, Irwin, PA (US); Shane S Volpe, Saltsburg, PA (US); Jason T Whiting, Gibsonia, PA (US); Gregory R Frank, Mt. Lebanon, PA (US); Rachel H Carlson, Falls Creek, PA (US); Gary A Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 17/649,574

(22) Filed: Feb. 1, 2022

(65) Prior Publication Data
US 2022/0257960 A1    Aug. 18, 2022

Related U.S. Application Data

(63) Continuation of application No. 16/543,822, filed on Aug. 19, 2019, now Pat. No. 11,266,846, which is a
(Continued)

(51) Int. Cl.
*A61N 1/39* (2006.01)
*A61B 5/00* (2006.01)
(Continued)

(52) U.S. Cl.
CPC ............ *A61N 1/3937* (2013.01); *A61B 5/318* (2021.01); *A61B 5/48* (2013.01); *A61B 5/1113* (2013.01); *A61B 5/1118* (2013.01)

(58) Field of Classification Search
CPC ..... A61N 1/3937; A61B 5/111; A61B 5/1113; A61B 5/48; A61B 5/0402
See application file for complete search history.

(56) References Cited

U.S. PATENT DOCUMENTS 3,534,727 A    10/1970  Roman
3,553,651 A     1/1971  Bird et al.
(Continued)

FOREIGN PATENT DOCUMENTS

EP    1642616    4/2006
EP    1455640    1/2008
(Continued)

OTHER PUBLICATIONS

American Journal of Respiratory and Critical Care Medicine, vol. 166, pp. 111-117 (2002). American Thoracic Society, ATS Statement: Guidelines for the Six-Minute Walk Test, available at http://www.atsjournals.org/doi/pdf/10.1164/ajrccm.166.1.at1102.
(Continued)

*Primary Examiner* — Alyssa M Alter
(74) *Attorney, Agent, or Firm* — ZOLL Medical Corporation

(57) ABSTRACT

An external wearable defibrillator for monitoring a patient for cardiac-related events is provided. The defibrillator includes ECG sensors configured to be disposed about a torso of the patient, therapy electrodes, and at least one motion sensor. The ECG sensors, therapy electrodes, and at least one motion sensor are configured to be worn continuously for an extended period of time. The defibrillator includes a wearable medical device controller including at least one processor configured to receive ECG data, receive motion data, identify at least one of ventricular tachycardia or ventricular fibrillation, initiate a treatment protocol including a defibrillation shock, and, using at least one of the ECG data or the motion data, identify a predetermined
(Continued)

pattern for syncope. The predetermined pattern includes bradycardia. The at least one processor is further configured to record the predetermined pattern in a memory and perform an intervening action to address the predetermined pattern.

20 Claims, 4 Drawing Sheets

Related U.S. Application Data continuation of application No. 15/729,212, filed on Oct. 10, 2017, now Pat. No. 10,441,804, which is a continuation of application No. 13/907,406, filed on May 31, 2013, now Pat. No. 9,814,894.

(60) Provisional application No. 61/653,844, filed on May 31, 2012.

(51) Int. Cl.
*A61B 5/318* (2021.01)
*A61B 5/11* (2006.01)

(56) References Cited

U.S. PATENT DOCUMENTS

| | | | |
|---|---|---|---|
| 4,094,310 A | 6/1978 | McEachern et al. |
| 4,136,690 A | 1/1979 | Anderson et al. |
| 4,422,459 A | 12/1983 | Simson |
| 4,458,691 A | 7/1984 | Netravali |
| 4,632,122 A | 12/1986 | Johansson et al. |
| 4,928,690 A | 5/1990 | Heilman et al. |
| 4,991,217 A | 2/1991 | Garrett et al. |
| 5,000,189 A | 3/1991 | Throne et al. |
| 5,062,834 A | 11/1991 | Gross et al. |
| 5,078,134 A | 1/1992 | Heilman et al. |
| 5,243,978 A | 9/1993 | Duffin, Jr. |
| 5,330,505 A | 7/1994 | Cohen |
| 5,342,404 A | 8/1994 | Alt et al. |
| 5,348,008 A | 9/1994 | Bornn et al. |
| 5,357,696 A | 10/1994 | Gray et al. |
| 5,381,798 A | 1/1995 | Burrows |
| 5,472,453 A | 12/1995 | Alt |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,827,196 A | 10/1998 | Yeo et al. |
| 5,887,978 A | 3/1999 | Lunghofer et al. |
| 5,924,979 A | 7/1999 | Swedlow et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,047,203 A | 4/2000 | Sackner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,387 B1 | 1/2001 | Kaib |
| 6,253,099 B1 | 6/2001 | Oskin et al. |
| 6,280,461 B1 | 8/2001 | Glegyak et al. |
| 6,406,426 B1 | 6/2002 | Reuss et al. |
| 6,546,285 B1 | 4/2003 | Owen et al. |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,908,437 B2 | 6/2005 | Bardy |
| 6,944,498 B2 | 9/2005 | Owen et al. |
| 6,961,612 B2 | 11/2005 | Elghazzawi et al. |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,712,373 B2 | 5/2010 | Nagle et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 9,814,894 B2 * | 11/2017 | Kaib ................. A61B 5/48 |
| 10,441,804 B2 * | 10/2019 | Kaib ................. A61N 1/3937 |
| 11,266,846 B2 * | 3/2022 | Kaib ................. A61B 5/48 |
| 2002/0004670 A1 | 1/2002 | Florio et al. |
| 2003/0004547 A1 | 1/2003 | Owen et al. |
| 2003/0032988 A1 | 2/2003 | Fincke |
| 2003/0055460 A1 | 3/2003 | Owen et al. |
| 2003/0095648 A1 | 5/2003 | Kaib et al. |
| 2003/0109904 A1 | 6/2003 | Silver et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0007970 A1 | 1/2004 | Ma et al. |
| 2004/0049233 A1 | 3/2004 | Edwards |
| 2004/0143297 A1 | 7/2004 | Ramsey, III |
| 2004/0162510 A1 | 8/2004 | Jayne et al. |
| 2004/0249419 A1 | 12/2004 | Chapman et al. |
| 2005/0049515 A1 | 3/2005 | Misczynski et al. |
| 2005/0131465 A1 | 6/2005 | Freeman et al. |
| 2005/0144043 A1 | 6/2005 | Holland et al. |
| 2005/0246199 A1 | 11/2005 | Futch |
| 2005/0283198 A1 | 12/2005 | Haubrich et al. |
| 2006/0036292 A1 | 2/2006 | Smith et al. |
| 2006/0085049 A1 | 4/2006 | Cory et al. |
| 2006/0095091 A1 | 5/2006 | Drew |
| 2006/0178706 A1 | 8/2006 | Lisogurski et al. |
| 2006/0211934 A1 | 9/2006 | Hassonjee et al. |
| 2006/0220809 A1 | 10/2006 | Stigall et al. |
| 2006/0253042 A1 | 11/2006 | Stahmann et al. |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0143864 A1 | 6/2007 | Cabana et al. |
| 2007/0161913 A1 | 7/2007 | Farrell et al. |
| 2007/0169364 A1 | 7/2007 | Townsend et al. |
| 2007/0196320 A1 | 8/2007 | Yasin |
| 2007/0197878 A1 | 8/2007 | Shklarski |
| 2007/0239214 A1 | 10/2007 | Cinbis |
| 2007/0239220 A1 | 10/2007 | Greenhut et al. |
| 2007/0265671 A1 | 11/2007 | Roberts et al. |
| 2008/0021532 A1 | 1/2008 | Kveen et al. |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0097793 A1 | 4/2008 | Dicks et al. |
| 2008/0103402 A1 | 5/2008 | Stickney et al. |
| 2008/0167535 A1 | 7/2008 | Stivoric et al. |
| 2008/0177341 A1 | 7/2008 | Bowers |
| 2008/0183090 A1 | 7/2008 | Farringdon |
| 2008/0249591 A1 | 10/2008 | Gaw et al. |
| 2008/0287749 A1 | 11/2008 | Reuter |
| 2008/0294019 A1 | 11/2008 | Tran |
| 2008/0306560 A1 | 12/2008 | Macho et al. |
| 2008/0306562 A1 | 12/2008 | Donnelly et al. |
| 2008/0312520 A1 | 12/2008 | Rowlandson et al. |

(56) References Cited

U.S. PATENT DOCUMENTS

| | | |
|---|---|---|
| 2008/0312522 A1 | 12/2008 | Rowlandson et al. |
| 2008/0312709 A1 | 12/2008 | Volpe et al. |
| 2009/0018428 A1 | 1/2009 | Dias et al. |
| 2009/0066366 A1 | 3/2009 | Solomon |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076559 A1 | 3/2009 | Libbus et al. |
| 2009/0093687 A1 | 4/2009 | Telfort et al. |
| 2009/0118808 A1 | 5/2009 | Belacazar et al. |
| 2009/0138059 A1 | 5/2009 | Ouwerkerk |
| 2009/0146822 A1 | 6/2009 | Soliman |
| 2009/0212984 A1 | 8/2009 | Baker |
| 2009/0231124 A1 | 9/2009 | Klabunde et al. |
| 2009/0232286 A1 | 9/2009 | Hurwitz |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0318779 A1 | 12/2009 | Tran |
| 2009/0326356 A1 | 12/2009 | Kracker |
| 2010/0010559 A1 | 1/2010 | Zhang et al. |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0081962 A1 | 4/2010 | Hamaguchi et al. |
| 2010/0114243 A1 | 5/2010 | Nowak et al. |
| 2010/0171611 A1 | 7/2010 | Gao et al. |
| 2010/0228103 A1 | 9/2010 | Schecter |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0015533 A1 | 1/2011 | Cox et al. |
| 2011/0022105 A9 | 1/2011 | Owen et al. |
| 2011/0093840 A1 | 4/2011 | Pynenburg et al. |
| 2011/0098765 A1 | 4/2011 | Patel |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0046558 A1 | 2/2012 | Virag et al. |
| 2012/0053479 A1 | 3/2012 | Hopenfeld |

FOREIGN PATENT DOCUMENTS

| | | |
|---|---|---|
| EP | 1720446 | 7/2010 |
| JP | 2000051371 | 2/2000 |
| JP | 2002514107 | 5/2002 |
| JP | 2002200059 | 7/2002 |
| JP | 2008302225 | 12/2008 |
| JP | 2009518153 | 5/2009 |
| JP | 2009521865 | 6/2009 |
| WO | 2004067083 | 8/2004 |
| WO | 2004078259 | 9/2004 |
| WO | 2005082454 | 9/2005 |
| WO | 2006050325 | 5/2006 |
| WO | 2007019325 | 2/2007 |
| WO | 2009034506 | 3/2009 |
| WO | 2010025432 | 3/2010 |
| WO | 2010077997 | 7/2010 |

OTHER PUBLICATIONS

Association for the Advancement of Medical Instrumentation, ANSI/AAMI DF80:2003 Medical Electrical Equipment—Part 2-4: Particular Requirements for the Safety of Cardiac Defibrillators (Including Automated External Defibrillators) 2004, ISBN 1-57020-210-9; abstract; p. vi; p. 50, section 107.1.2.

De Bock et al., "Captopril treatment of chronic heart failure in the very old," J. Gerontol. (1994) 49: M148-M152.

Extended European Search Report from corresponding EP Application No. 13797885.4 dated Feb. 10, 2016.

International Search Report and Written Opinion from corresponding International Application No. PCT/US2013/043719 dated Sep. 4, 2013.

O'Keeffe et al., "Reproducibility and responsiveness of quality of life assessment and six minute walk test in elderly heart failure patients," Heart (1998) 80: 377-382.

\* cited by examiner

SYSTEMS AND METHODS FOR DETECTING HEALTH DISORDERS

RELATED APPLICATIONS

This application claims priority under 35 U.S.C. § 120 as a continuation of U.S. application Ser. No. 16/543,822, entitled "SYSTEMS AND METHODS FOR DETECTING HEALTH DISORDERS," filed on Aug. 19, 2019, now U.S. Pat. No. 11,266,846, which claims priority under 35 U.S.C. § 120 as a continuation of U.S. application Ser. No. 15/729,212, entitled "SYSTEMS AND METHODS FOR DETECTING HEALTH DISORDERS," filed on Oct. 10, 2017, now U.S. Pat. No. 10,441,804, which claims priority under 35 U.S.C. § 120 as a continuation of U.S. application Ser. No. 13/907,406, titled "SYSTEMS AND METHODS FOR DETECTING HEALTH DISORDERS," filed on May 31, 2013, now U.S. Pat. No. 9,814,894, which claims priority under 35 U.S.C. § 119(e) to U.S. Provisional Application Ser. No. 61/653,844, titled "SYSTEMS AND METHODS FOR DETECTING HEALTH DISORDERS," filed on May 31, 2012, each of which is hereby incorporated herein by reference in its entirety.

BACKGROUND

Technical Field

Aspects of the present invention relate to medical devices, and more particularly to apparatus and methods for detecting disorders and symptoms caused at least in some instances by abnormal activity within the cardiovascular system.

Discussion of Related Art

Syncope may be defined as a transient loss of consciousness resulting from an insufficient presence of oxygen in the brain. Typical symptoms progress through dizziness, clamminess of the skin, a dimming of vision or greyout, possibly tinnitus, complete loss of vision, weakness of limbs, and physical collapse. Syncope can be caused by a number of cardiovascular, neurological, or other factors.

Although a syncopal event itself is not fatal by definition, the event may be indicative of underlying cardiovascular dysfunction which can involve a high risk for the patient to suffer a life-threatening arrhythmia, such as ventricular tachycardia, ventricular fibrillation, bradycardia, or asystole.

Since loss of consciousness can be a symptom for a variety of conditions, the patient requires a thorough examination and testing in order to determine the cause of syncope. Traditional methods of evaluating a patient who presents with syncope include a blood test, a tilt table test, an electrocardiogram ("ECG"), or a heart monitor (e.g., a holter monitor, loop recorder, or event recorder). When performing the tilt table test, the patient is strapped to a table, the table and the patient are reoriented from a lying to standing position, and the patient is observed to determine if syncope is triggered by body position.

When using a holter monitor, loop recorder or event recorder, the device records the heart rhythm during daily activities over a period of time. Some recorders allow the patient to place markers on recordings when certain events occur or allow the patient to trigger a recording. These types of devices are typically worn between 1 and 60 days.

In many cases, the exact cause of syncope may go undetected. Syncope may occur randomly, and it may not be possible to duplicate in a monitored setting.

SUMMARY

Embodiments disclosed herein utilize a non-invasive ambulatory device capable of defibrillation (e.g., a wearable defibrillator or some other electrotherapy device) to monitor for and detect events associated with cardiovascular instability, such as syncope, caused at least in some instances by an abnormality within the cardiovascular system. For instance, according to some embodiments, a patient who presents with syncope is fitted with a wearable defibrillator. In these embodiments, the wearable defibrillator monitors and records data descriptive of the patient's activities and physiology.

In other embodiments, the wearable defibrillator analyzes the recorded data in near real time. In these embodiments, responsive to detecting a pattern of data associated with a symptom, the wearable defibrillator may address the symptom by performing one or more intervening actions. Examples of these intervening actions include treating the cause underlying the symptom and notifying an external entity (e.g., the patient, a bystander, a caregiver, a medical professional, or another computer system) of the detected symptom associated with data pattern.

Other embodiments manifest an appreciation that conventional tests, such as the tilt test, are often ineffective in revealing the cause of syncope, and due to the fact that syncope is a random, transient, and relatively low frequency event even for a patient who is susceptible to it, it may require many days or weeks of monitoring before the syncope causes can be recorded, detected and treated. Patients are usually hospitalized for a couple of days to perform testing to rule out certain, specific conditions; however, it would be too expensive to keep all patients with possible syncope in the hospital to be monitored for longer periods. Therefore, patients will be fitted with one of the above-described monitoring devices and discharged from the hospital until either the nature of the syncopal event is defined, or the treating physician deems it to be no longer of value. As mentioned previously, when a patient is discharged from the hospital, they are at risk of potentially fatal events due to the syncope or its underlying physiological cause.

Unfortunately, the current state of the art, as discussed above, only provides for the monitoring and recording of these syncopal episodes, but does not provide any means of protecting the patient who has been released from the hospital with a recording device, but who is essentially unprotected from risk of mortality due to the underlying causes of syncope.

Also, due to the large number of patients encountering syncope, as well as the high risk profile for the implantation of implantable pacer/cardioverter defibrillators (ICDs), these patients are not candidates for the widespread implantation of ICDs as a prophylactic measure in the short term.

It would thus be desirable to have a system incorporating a wearable therapeutic device that is comfortable to wear continuously for extended periods that could both detect the onset of incipient syncope prior to loss of consciousness, as well as treat other manifestations of the underlying condition and prevent the actual occurrence of the syncope itself, and treat cardiac dysfunction.

According to some embodiments, a method of treating a patient presenting with syncope is provided. The method includes acts of detecting, by a wearable defibrillator, an event associated with syncope; storing, by the wearable defibrillator, data descriptive of the event in association with an indication that the data includes data descriptive of a syncopal event; and addressing the event.

In the method, the act of detecting the event may include an act of detecting a cardiac arrhythmia. The act of detecting the cardiac arrhythmia may include an act of detecting at least one of ventricular tachycardia, ventricular fibrillation, and bradycardia and the act of addressing the event may include issuing a therapeutic treatment. The act of issuing the therapeutic treatment may include an act of issuing at least one of a pacing pulse and a defibrillation shock. The act of addressing the event may include an act of issuing a notification to the patient and bystanders.

In the method, the act of detecting the event may include an act of identifying a pattern of data including data received from a plurality of sensors. The act of identifying the pattern of data may include identifying a pattern of data including data received from at least one of an electrocardiogram sensor and a motion sensor.

According to other embodiments, a wearable medical device capable of treating a patient presenting with syncope is provided. The wearable medical device includes a memory storing event profile information, a battery, at least one treatment electrode coupled to the battery, at least one processor coupled to the memory and the at least one treatment electrode, and an event manager executed by the at least one processor. The event manager is configured to detect an event associated with syncope; store, in the memory, data descriptive of the event in association with an indication that the data includes data descriptive of a syncopal event; and address the event.

In the device, the event that the event manager is configured to detect may include a cardiac arrhythmia. The cardiac arrhythmia may be bradycardia and the event manager may be configured to address the event by issuing a therapeutic treatment. The event manager may be configured to issue the therapeutic treatment by issuing at least one of a pacing pulse and a defibrillation shock. The event manager may be configured to address the event by issuing a notification to the patient.

In the device, the event manager may be configured to detect the event by identifying a pattern of data including data received from a plurality of sensors. The event manager may be configured to identify the pattern of data by identifying a pattern of data that includes data received from at least one of an electrocardiogram sensor and a motion sensor. The event profile information may include information descriptive of the pattern of data.

According to another embodiment, a method for protecting a patient presenting with syncope from cardiac dysfunction is provided. The patient may have been diagnosed as having experienced (a) cardiac syncope or (b) undiagnosed syncope, for which a diagnosis of cardiac syncope cannot be clearly dismissed. Patients likely to be diagnosed as such include, but are not limited to, patients meeting one or more of the following criteria: a history, or family history, of cardiovascular disease (e.g. coronary artery disease, heart failure, structural heart disease); abnormal ECG findings (e.g. ischemia, dysrhythmias, conduction abnormalities); advanced age; and low hematocrit count. The method includes identifying a syncopal event within the patient's history, and providing, responsive to identifying the syncopal event, the patient with a wearable defibrillator. The method may expressly exclude protecting a patient presenting with syncope who has been definitively diagnosed as having experienced non-cardiac syncope, including but not limited to patients having suffered one of the following: vasovagal syncope; orthostatic syncope; carotid sinus syncope; drug-related syncope; and seizure.

The method may further include an act of monitoring the patient's physiology via the wearable defibrillator. The method may further include an act of contacting the patient where monitoring reveals the presence of an arrhythmia.

In the method, the act of providing the patient with the wearable defibrillator may not be responsive to a diagnosis of cardiac dysfunction. The act of providing the patient with the wearable defibrillator may include an act of providing the patient with a wearable defibrillator configured to exclusively identify and treat cardiac dysfunction. The act of providing the patient with the wearable defibrillator may include an act of providing the patient with a wearable defibrillator that includes a long term wear electrode.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed subject matter. References to "an embodiment," "some embodiments," "an alternate embodiment," "various embodiments," "one embodiment," "at least one embodiments," "this and other embodiments" or the like are not necessarily mutually exclusive and are intended to indicate that a particular feature, structure, or characteristic described in connection with the embodiment and may be included in that embodiment and other embodiments. The appearances of such terms herein are not necessarily all referring to the same embodiment.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Figure 1:
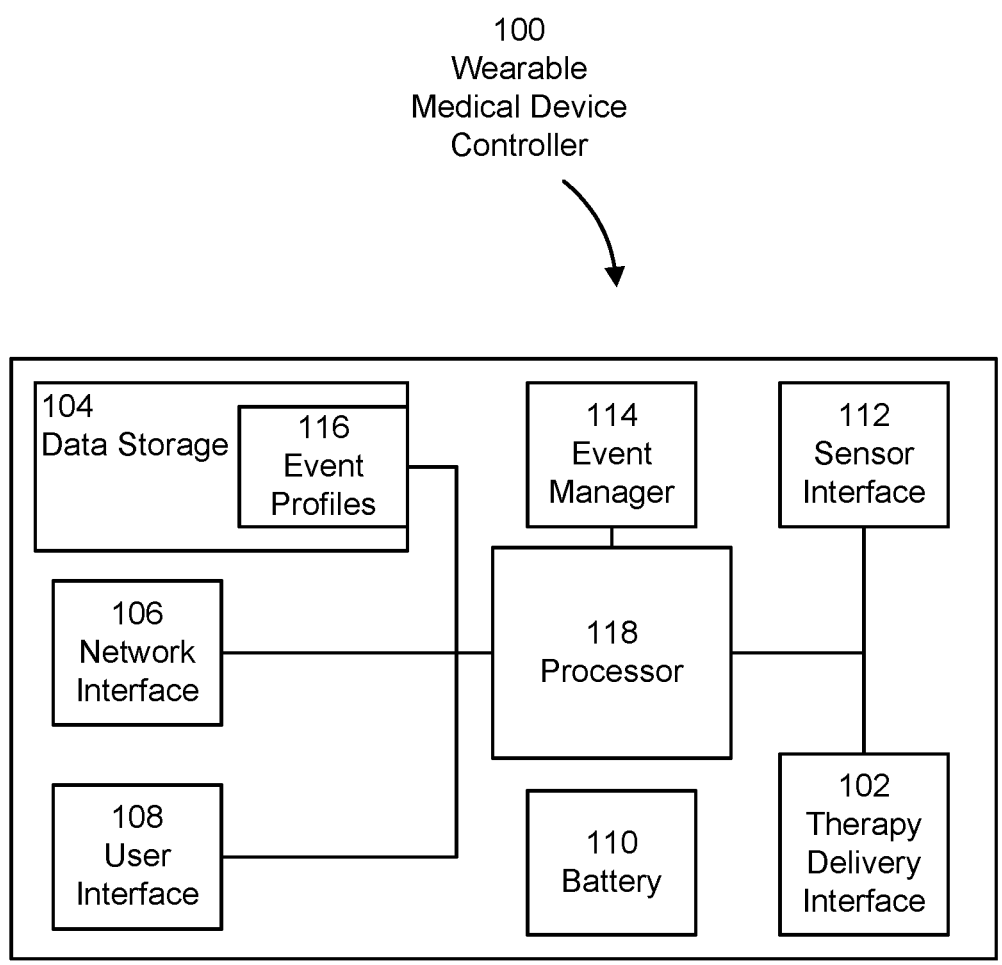
FIG. 1 is a schematic of one example of a wearable medical device controller.

Aspects and embodiments disclosed herein relate to apparatus and processes for detecting, recording, and treating health disorders and symptoms that are known to have many potential root causes. For instance, in at least one embodiment, a patient presenting with a symptom, such as syncope, having many potential causes is fitted with a wearable defibrillator that is configured to record data descriptive of the patient's physiology and physical activities. In this embodiment, the recorded data is analyzed to determine one or more root causes of the symptom.

For instance, the recorded data may be analyzed for aberrant patterns that indicate abnormal physiological function. These aberrant patterns may occur prior to, during, or after the onset of symptoms. Furthermore, the aberrant patterns may include information that is descriptive of various physical phenomena gathered across a variety of sensors. If aberrant patterns are found during this analysis, correct diagnosis of the root cause or causes of the symptom may be expedited, thereby allowing the patient to be quickly treated specifically for cause of the symptom. In addition, if the aberrant patterns were not previously known to be indicative of a potential root cause of the symptom, the aberrant patterns may be added to a catalogue of predetermined patterns associated with a symptom.

More specifically, in some embodiments, a wearable electrotherapy device is equipped with a near infra-red spectroscopy system for measurement of parameters such as tissue oxygenation, pH and glucose levels. One example of such a spectroscopy system is manufactured by Reflectance Medical. The spectroscopy system may be utilized to provide an early warning of impending decompensation of the sympathetic nervous system regulation of hemodynamics and heart function. If sympathetic tone is found to be lacking, the wearable electrotherapy device may initiate electrical therapy specifically designed to target the sympathetic tone of the heart. One example of such a therapy is referred to as packet therapy, which is a pulse train of high frequency DC pulses that provide pacing as well as stimulation of the sympathetic tone of the myocardium. One form of packet therapy is described further in application Ser. No. 10/868,395, entitled "MICROPERFUSIVE ELECTRICAL STIMULATION," filed Jun. 15, 2004 (now U.S. Pat. No. 8,805,491), which is hereby incorporated herein by reference in its entirety.

Degradation of a patient's condition into syncope is typically multifaceted as well as extending over a period of time. Earlier warnings of a potentially weakened condition may be evidenced by depressed metabolic reserve, as evidenced by an overly depressed pH level as a function of activity level. Therefore, some embodiments include an electrotherapy device that incorporates one or more motion sensors. In these embodiments, the electrotherapy device may calculate an activity level and then the pH and other metabolic measures such as mitochondrial respiration can be correlative to the activity level. In this way, metabolic reserve can be roughly estimated, by the electrotherapy device, as the ration of the metabolic state divided by the activity level. In addition, in some embodiments, the electrotherapy device calculates a baseline metabolic reserve for each patient at the time they are fitted with the electrotherapy device. If during the course of use, the electrotherapy device determines that the metabolic reserve has significantly degraded then further action may be taken by the electrotherapy device. Examples of further action that may be taken include issuing a warning to the patient, sending a communication via cell or wireless to the patient's doctor, or even possibly initiating some adjunctive electrical therapy like packet pacing.

Patients with diabetes may also be further at risk of syncopal episodes due to reduced blood glucose levels. Therefore, some embodiments of the electrotherapy device measure blood glucose levels to provide early warning to the patient of this potentially dangerous condition so that they can take the necessary steps of prevention.

Multiple motion sensors may be incorporated into some embodiments including the electrotherapy device in such a way that a complete three dimensional model is created of the patient's torso, and also, in some examples, of the limbs and head. By monitoring the three-dimensional motion of the body, earlier symptoms of balance loss can be detected by these embodiments in advance of the full syncopal episode. Subtle changes such as disregulation of verticality (swaying of the body) can be detected prior to a patient's loss of consciousness.

Some embodiments include an electrotherapy device that comprises stimulating electrodes located proximate to regions of the patient's body that are designed to primarily stimulate the nervous system, rather than the myocardium. For instance, in one embodiment, electrodes may be placed on the neck in locations such that, when activated, cause stimulation current to flow across the superior cervical ganglia. The electrodes may vary in size and shape. In one embodiment, the electrode is an elongated strip 1"×3" in length, configured in a butterfly configuration, with the anode and cathode at opposite ends of the strip. The strip is positioned with the vertical axis of the cervical ganglion centered between the two stimulating electrodes. The electrodes are placed during fitting of the device. The electrotherapy device may conduct a test to determine if the electrodes are positioned to stimulate primarily the cervical ganglion or other sympathetic nervous system nerve (as opposed to vagal) and the electrodes may be repositioned if this is not the case.

In some embodiments, if any of the above-mentioned conditions are encountered, then the electrotherapy device may apply varying degrees of stimulation to the nerves. Initially, the stimulation may be at a relatively low level, so as not to cause discomfort, surprise or panic in the patient.

In other embodiments, the electrotherapy device may include an additional set of electrodes placed to stimulate primarily vagal nerves.

In other embodiments, the wearable defibrillator transmits recorded data to a remote server via a network interface, such as the network interface 106 described below with reference to FIG. 1. In these embodiments, a large volume of recorded data is accumulated on the remote server over a prolonged period of time (e.g., weeks or months). This large volume of data may be analyzed using a variety of techniques to extract knowledge regarding the root cause or causes of a patient's symptoms. The analysis techniques used to mine this data may include correlation analysis, data variable comparisons, sandbox playing, discovery processes, iterative testing, looking for relations, subtraction, injection, and timeline matchup. In other embodiments, the data is recorded on removable data storage, such as an SD card, which may be removed from the device. This embodiment may be especially well suited for collecting and providing large volumes of recorded data.

In other embodiments, the wearable defibrillator is configured to use the catalogue of predetermined patterns to analyze the recorded data and identify predetermined patterns within the data that are associated with syncope or other symptoms. In these embodiments, the wearable defibrillator is configured to, after identifying one or more predetermined patterns associated with a symptom, perform intervening actions to address the symptom.

In another embodiment, the wearable defibrillator is configured in accord with the wearable defibrillator described in application Ser. No. 13/109,382, entitled "WEARABLE AMBULATORY MEDICAL DEVICE WITH MULTIPLE SENSING ELECTRODES," filed May 17, 2011 (now U.S. Pat. No. 8,706,215), which is hereby incorporated herein by reference in its entirety. In other embodiments, a control unit of the wearable defibrillator includes a set of components configured to perform the processes described herein. This set of components may include hardware components or a combination of hardware and software components.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Wearable Medical Device Controller

FIG. 1 illustrates a wearable medical device controller 100 that is configured to monitor a patient and the patient's environment for events of interest, to record these events, and to intervene, where appropriate, by treating the patient or issuing a notification to an external entity, such as a person (e.g., patients, physicians, and monitoring personnel) or another computer system (e.g., monitoring systems or emergency response systems). As shown in FIG. 1, the wearable medical device controller 100 includes a processor 118, a sensor interface 112, an event manager 114, a therapy delivery interface 102, data storage 104, a communication network interface 106, a user interface 108 and a battery 110. The data storage 104 includes event profile information 116 and other event information. In some embodiments, the data storage 104 includes sufficient capacity to store 2 or more weeks of physiological information. In other embodiments, the data storage 104 may be removable. Further, in this illustrated example, the battery 110 is a rechargeable 3 cell 2200 mAh lithium ion battery pack that provides electrical power to the other device components with a minimum 24 hour runtime between charges.

According to the example illustrated in FIG. 1, the processor 118 is coupled to the sensor interface 112, the therapy delivery interface 102, the data storage 104, the network interface 106 and the user interface 108. The processor 118 performs a series of instructions that result in manipulated data which is stored in and retrieved from the data storage 104. According to a variety of examples, the processor 118 is a commercially available processor such as a processor manufactured by Texas Instruments, Intel, AMD, Sun, IBM, Motorola, Freescale and ARM Holdings. However, the processor 118 may be any type of processor, multiprocessor or controller, whether commercially available or specially manufactured. For instance, according to one example, the processor 118 may include a power conserving processor arrangement such as described in application Ser. No. 12/833,096, entitled "SYSTEM AND METHOD FOR CONSERVING POWER IN A MEDICAL DEVICE," filed Jul. 9, 2010 (now U.S. Pat. No. 8,904,214) (hereinafter the "'096 application"), which is hereby incorporated herein by reference in its entirety. In another example, the processor 118 is an Intel® PXA270.

In addition, in several examples the processor 118 is configured to execute a conventional real-time operating system ("RTOS"), such as RTLinux. In these examples, the RTOS may provide platform services for application software, such as some examples of the event manager 114, which is discussed further below. These platform services may include inter-process and network communication, file system management and standard database manipulation. However, one of many operating systems may be used, and examples are not limited to any particular operating system or operating system characteristic. For instance, in some examples, the general purpose processor 102 may be configured to execute a non real time operating system, such as BSD or GNU/Linux.

The event manager 114 is configured to manage event profiles, such as event profiles specified in the event profile information 116, to detect events according to predetermined patterns and comparison rules included in the event profiles, and to process events according to logic included in the event profile. The event profiles may specify that events be identified based on a variety of predetermined patterns of data including data representative of the patient's physical condition and data representative of the patient's behavior.

For example, one or more event profiles may specify that the event manager 114 record an event after receiving an indication that an external entity, such as a patient, has interacted with the user interface 108 in one or more predetermined ways (e.g., the user presses a particular response button). For instance, according to one embodiment, the user interface 108 includes a response button designated to record a syncopal event. In this embodiment, an event profile specifies that the event manager 114 record a syncopal event after receiving an indication that an external entity has pressed the syncope response button. According to one exemplary usage scenario, a patient may press the syncope response button when encountering a prodrome associated with syncope, such as lightheadedness or dizziness. Other user-identified events configured to record data representative of other symptoms or disorders may be recorded in this manner. In recording the events, the event manager 114 may store records of the events in the data storage 104. Such recordings may provide valuable evidence of clinically significant events that may otherwise be missed.

In another example, an event profile specifies that the event manager 114 record an event after identifying a predetermined pattern for tachycardia, which is an abnormally fast heart rhythm, within data received via the sensor interface 112. According to this example, the event profile further specifies that the event manager 114 initiate a treatment protocol that may result in a defibrillation shock of approximately 150 Joules being administered to the patient via the therapy delivery interface 102 to treat the tachycardia.

In another example, an event profile specifies that the event manager 114 record an event after identifying a predetermined pattern for ventricular fibrillation, which is a severely abnormal heart rhythm, within data received via the sensor interface 112. According to this example, the event profile further specifies that the event manager 114 initiate a treatment protocol that may result in a defibrillation shock being administered to the patient via the therapy delivery interface 102 to treat the ventricular fibrillation.

In another example, an event profile specifies that the event manager 114 record an event after identifying a predetermined pattern for bradycardia, which is an abnormally slow heart rhythm, within data received via the sensor interface 112. According to this example, the event profile further specifies that the event manager 114 initiate a treatment protocol that may result in a therapeutic treatment being administered to the patient via the therapy delivery interface 102 to treat the bradycardia. Examples of this therapeutic treatment include a pacing pulse and a defibrillation shock.

In another example, an event profile specifies that the event manager 114 record an event after identifying a predetermined pattern for a precursor of syncope within data received via the sensor interface 112. This predetermined pattern may be indicative of any combination of a number of physical phenomena such as central nervous system ischemia, low blood pressure, hypoglycemia, a vasovagal response, an abnormal heart rate, an abnormal variability in heart rate, a cardiac arrhythmia (e.g., tachycardia or bradycardia, among others), a pulmonary embolism, a change in the patient's gait, increased swaying when the patient walks, excessive coughing by the patient, increased sweating by the patient. According to this example, the event profile further specifies that the event manager 114 notify an external entity that an episode of syncope may be imminent. Examples of the types of notifications that the event manager 114 may initiate are described in application Ser. No. 13/428,703, entitled "SYSTEM AND METHOD FOR ADAPTING ALARMS IN A WEARABLE MEDICAL DEVICE," filed Mar. 23, 2012 (now U.S. Pat. No. 9,135,398), which is hereby incorporated herein by reference in its entirety. The external entities notified may include the patient, the patient's physician, or the patient's caregiver and the notification may include prompts instructing the external entity to take a particular course of action. In one example, the notification prompts the patient to sit down or call of help, thereby preventing a potential fall. According to another example, a notification is issued to a patient to prevent a syncope episode. In this example, the notification is designed to cause a physiological response, such as a startle response, in the patient that averts the syncope episode.

In another example, an event profile specifies that the event manager 114 record an event after identifying a predetermined pattern for stroke within data received via the sensor interface 112. According to this example, the event profile further specifies that the event manager 114 initiate a testing protocol via the user interface 108 that presents the patient with an on-screen questionnaire configured to determine whether the patient has suffered a stroke. The testing protocol may further include a reaction time measurement to further aid in determining whether a stroke event has occurred.

It is to be appreciated that any event profile may further specify that the event manager 114 initiate a responsiveness test. According to one exemplary responsiveness test, the event manager 114 issues a notification lasting a predetermined period of time, (e.g., at least 25 seconds) and awaits a target response. This target response may include actuation of one or more response buttons that are a part of the wearable defibrillator. Further, according to this example, if the target response is received, but the response buttons do not remain actuated (perhaps signaling that the patient has lost consciousness), the event manager 114 reissues the notification. The notification includes audible tones that escalate in volume, followed by voice warnings to bystanders indicating that a therapeutic shock is imminent. After completing the notification, the event manger 114 may initiate a treatment protocol, which may result in a therapeutic shock or which may be aborted where an abnormality resolves or another patient response is received prior to delivery of the therapeutic shock.

The event manager 114 may be implemented using hardware or a combination of hardware and software. For instance, in one embodiment, the event manager 114 is implemented as a software component that is stored within the data storage 104 and executed by the processor 118. In this example, the instructions included in the event manager 114 program the processor 118 to configure event profiles and detect events using the event profiles. In other examples, event manager 114 may be an application-specific integrated circuit ("ASIC") that is coupled to the processor 118 and tailored to manage event profiles and detect events using events specified within the event profiles. Thus, embodiments of the event manager 114 are not limited to a particular hardware or software implementation. Specific examples of the processes performed by the event manager 114 are discussed further below with reference to FIGS. 3 and 4.

In some embodiments, the components disclosed herein, such as the event manager 114, may read parameters that affect the functions performed by the components. These parameters may be physically stored in any form of suitable memory including volatile memory, such as RAM, or nonvolatile memory, such as a magnetic hard drive. In addition, the parameters may be logically stored in a propriety data structure, such as a database or file defined by a user mode application, or in a commonly shared data structure, such as an application registry that is defined by an operating system. In addition, some embodiments provide for both system and user interfaces, as may be implemented using the user interface 108, that allow external entities to modify the parameters and thereby configure the behavior of the components.

For example, the event manager 114 includes a disorder mode parameter. The disorder mode parameter indicates a generalized set of preferences that the event manager 114 applies to determine if an event as occurred. In one embodiment, each disorder mode is associated one or more event profiles and the event manager 114 utilizes the current disorder mode to resolve which event profiles are active and which are inactive. In this embodiment, inbound, unprocessed data is compared against the active profiles to determine if an event has occurred. Example disorder modes include, but are not limited to, arrhythmia (the event manager 114 detects cardiac arrhythmias), syncope (the event manager 114 detects syncope), stroke (the event manager 114 detects stroke) and hybrid (the event manager 114 detects any combination of the previous disorders and symptoms).

The data storage 104 includes a computer readable and writeable nonvolatile data storage medium configured to store non-transitory instructions and other data. In addition, the data storage 104 includes a processor memory that stores data during operation of the processor 118. In some examples, the processor memory includes a relatively high performance, volatile, random access memory such as dynamic random access memory ("DRAM"), static memory ("SRAM") or synchronous DRAM. However, the processor memory may include any device for storing data, such as a non-volatile memory, with sufficient throughput and storage capacity to support the functions described herein. According to several examples, the processor 118 causes data to be read from the nonvolatile data storage medium into the processor memory prior to processing the data. In these examples, the processor 118 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system or data storage system.

The instructions stored on the data storage 104 may include executable programs or other code that can be executed by the processor 118. The data storage 104 also may include information that is recorded, on or in, the medium, and this information may be processed by the processor 118 during execution of instructions. More specifically, the information may be stored in one or more data structures specifically configured to conserve storage space or increase data exchange performance. The instructions may be persistently stored as encoded signals, and the instructions may cause the processor 118 to perform the functions described herein. The medium may, for example, be optical disk, magnetic disk or flash memory, among others, and may be permanently affixed to, or removable from, the wearable medical device controller 100.

The event profile information 116 includes data used by the event manager 114 to detect and process events. More particularly, according to the illustrated embodiment, the event profile information 116 includes information that defines patterns of data that are associated with events. Data conforming to these patterns may be received before, during, or after onset of any symptoms associated with a disorder. The received data underlying the patterns may include any data processed by the wearable medical device controller 100. However, in broad terms, data may be received and processed is descriptive of the patient's physical condition or behavior. The data may be received by a wide variety of components and thus descriptive of a wide variety of physical phenomenon. Examples of some components through which data may be acquired are described further below with reference to FIG. 2.

Common event characteristics include a pattern of data representative of the event, one or more symptoms associated with the event, one or more disorder modes in which the event manager 114 actively scans for and records the event, and one or more intervention processes to be performed upon detection of the event. Intervention processes may include diagnostic, reporting, and treatment processes that are specific to the event. Specific examples of intervention processes are described further below with reference to FIG. 4.

As illustrated in FIG. 1, the event manager 114 and the event profile information 116 are separate components. However, in other embodiments, the event manager 114 and the event profile information 116 are combined into a single component or re-organized so that a portion of the data included in the event manager 114, such as executable code that causes the processor 118 to adapt a detected event, resides in the event profile information 118, or vice versa. Such variations in these and the other components illustrated in FIG. 1 are intended to be within the scope of the embodiments disclosed herein.

The event profile information 116 may be stored in any logical construction capable of storing information on a computer readable medium including, among other structures, flat files, indexed files, hierarchical databases, relational databases or object oriented databases. In addition, various examples organize the event profile information 116 into particularized and, in some cases, unique structures to perform the functions disclosed herein. In these examples, the data structures are sized and arranged to store values for particular types of data.

As shown in FIG. 1, the wearable medical device controller 100 includes several system interface components 102, 106 and 112. Each of these system interface components is configured to exchange (i.e. send or receive) data with one or more specialized devices that may be located within the wearable medical device controller 100 or elsewhere. The components used by the interfaces 102, 106 and 112 may include hardware components, software components or a combination of both. In the instance of each interface, these components physically and logically couple the wearable medical device controller 100 to the specialized devices. This physical and logical coupling enables the wearable medical device controller 100 to both communicate with and, in some instances, control the operation of the specialized devices. These specialized devices may include physiological sensors, therapy delivery devices and computer networking devices.

According to various examples, the hardware and software components of the interfaces 102, 106 and 112 employ a variety of coupling and communication techniques. In some examples, the interfaces 102, 106 and 112 use leads, cables or other wired connectors as conduits to exchange data between the wearable medical device controller 100 and specialized devices. In other examples, the interfaces 102, 106 and 112 communicate with specialized devices using wireless technologies such as radio frequency or infrared technology. The software components included in the interfaces 102, 106 and 112 enable the processor 118 to communicate with specialized devices. These software components may include elements such as objects, executable code and populated data structures. Together, these software components provide software interfaces through which the processor 118 can exchange information with specialized devices. Moreover, in at least some embodiments where one or more specialized devices communicate using analog signals, the interfaces 102, 106 and 112 further include components configured to convert analog information into digital information, and vice-versa, to enable the processor 118 to communicate with specialized devices.

As discussed above, the system interface components 102, 106 and 112 shown in the example of FIG. 1 support different types of specialized devices. For instance, in some embodiments, the components of the sensor interface 112 couple the processor 118 to one or more physiological sensors such as a body temperature sensors, respiration monitors, dry capacitive ECG electrodes, adhesive electrodes, or EEG electrodes. These electrodes may include one or more long term wear electrodes that are configured to be continuously worn by a patient for extended periods (e.g., 3 or more days). One example of such a long term wear electrode is described in Application Ser. No. 61/653,749, entitled "LONG TERM WEAR MULTIFUNCTION BIOMEDICAL ELECTRODE," filed May 31, 2012, which is hereby incorporated herein by reference in its entirety. In other embodiments, the components of the sensor interface 112 couple the processor 118 to one or more environmental sensors such as atmospheric thermometers, airflow sensors, audio sensors, accelerometers, and hygrometers. It is to be appreciated that these sensors may include sensors with a relatively low sampling rate, such as wireless sensors.

The components of the therapy delivery interface 102 couple one or more therapy delivery devices, such as capacitors and defibrillator/pacer electrodes, to the processor 118. In addition, the components of the network interface 106 couple the processor 118 to a computer network via a networking device, such as a bridge, router or hub. According to a variety of examples, the network interface 106 supports a variety of standards and protocols, examples of which include USB (via, for example, a dongle to a computer), TCP/IP, Ethernet, Wireless Ethernet, Bluetooth, ZigBee, M-Bus, CAN-bus, IP, IPV6, UDP, DTN, HTTP, FTP, SNMP, CDMA, NMEA and GSM. To ensure data transfer is secure, in some examples, the wearable medical device controller 100 can transmit data via the network interface 106 using a variety of security measures including, for example, TLS, SSL or VPN. In other examples, the network interface 106 includes both a physical interface configured for wireless communication and a physical interface configured for wired communication. According to various embodiments, the network interface 106 enables communication between the wearable medical device controller 100 and a variety of personal electronic devices including computer enabled glasses and earpieces.

Thus, the various system interfaces incorporated in the wearable medical device controller 100 allow the device to interoperate with a wide variety of devices in various contexts. For instance, some examples of the wearable medical device controller 100 are configured to perform a process of sending critical events and data to a centralized server via the network interface 106. An illustration of a process in accord with these examples is disclosed in U.S. Pat. No. 6,681,003, entitled "DATA COLLECTION AND SYSTEM MANAGEMENT FOR PATIENT-WORN MEDICAL DEVICES" and issued on Jan. 20, 2004 which is hereby incorporated herein by reference in its entirety.

The user interface 108 shown in FIG. 1 includes a combination of hardware and software components that allow the wearable medical device controller 100 to communicate with an external entity, such as a user. These components are configured to receive information from actions such as physical movement, verbal intonation or thought processes. In addition, the components of the user interface 108 can provide information to external entities. Examples of the components that may be employed within the user interface 108 include keyboards, mouse devices, trackballs, microphones, electrodes, response buttons, touch screens, printing devices, display screens and speakers. In some examples, the electrodes include an illuminating element, such as an LED. In other examples, the printing devices include printers capable of rendering visual or tactile (Braille) output.

The wearable medical device controller 100 has a variety of potential applications and is well suited to devices that detect and process a variety of events, some of which require a predetermined response from the external entity. Predetermined responses may include any response that is appropriate given the event being reported. Predetermined responses may include acknowledgment of the event, entry of information indicating that the event is being addressed and rectification of the condition that triggered the event.

Examples of devices to which the wearable medical device controller 100 is well suited include critical care medical devices, such as a wearable external defibrillator. An example of one such defibrillator is described in the '096 application with reference to FIG. 3. In at least one example, the wearable defibrillator 300 illustrated in FIG. 3 of the '096 application employs the wearable medical device controller 100, as disclosed in the present application, as a substitute for the portable treatment controller 200 described in the '096 application. In this example, the ECG Electrodes and Therapy Pads illustrated in FIG. 3 of the '096 application are logically and physically coupled to the wearable medical device controller 100 via the sensor interface 112 and the therapy delivery interface 102, respectively.

Figure 2:
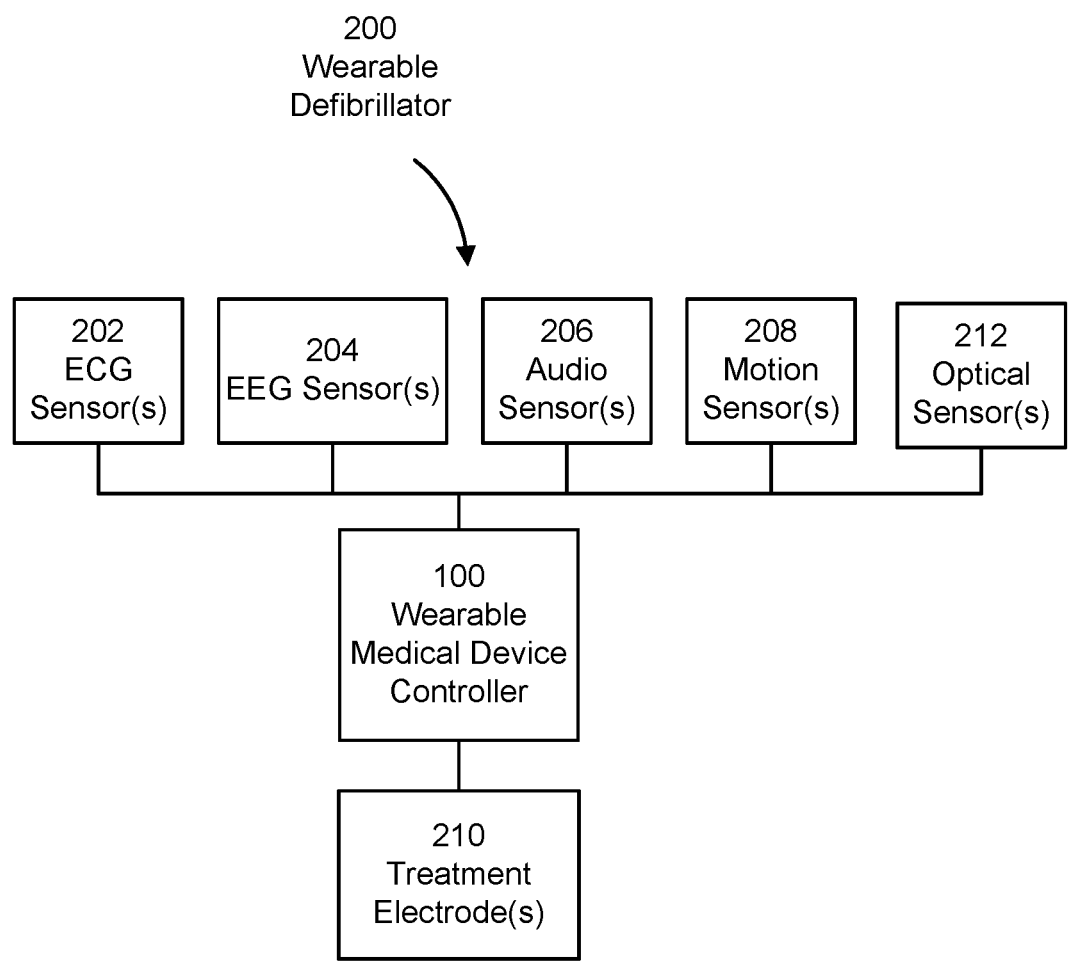
FIG. 2 is a schematic of an exemplary wearable defibrillator.

FIG. 2 illustrates an embodiment which utilizes the wearable medical device controller 100. As shown in FIG. 2, a wearable defibrillator 200 includes a wearable device controller 100, one or more ECG sensors 202, one or more EEG sensors 204, one or more audio sensors 206, one or more motion sensors 208, one or more optical sensors 212, and one or more treatment electrodes 210. In this embodiment, the wearable device controller 100 is logically and physically coupled to the treatment electrodes 210 via the therapy delivery interface 102. Further, in this embodiment, the wearable device controller 100 is logically and physically coupled to the ECG sensors 202, the EEG sensors 204, the audio sensors 206, the motion sensors 208, and the optical sensors via the sensor interface 112.

In some embodiments, the treatment electrodes 210 include a first therapy electrode and the second therapy electrode that are disposed on the front of a patient's torso. For example, the first therapy electrode may be externally located at the apex of the heart and the second therapy electrode may be located along the parasternal line. In other embodiments, the first therapy electrode is disposed on the front of the patient's torso and a second therapy electrode is disposed on the back of the patient's torso. Thus embodiments are not limited to a particular arrangement of treatment electrodes 210.

Figure 3:
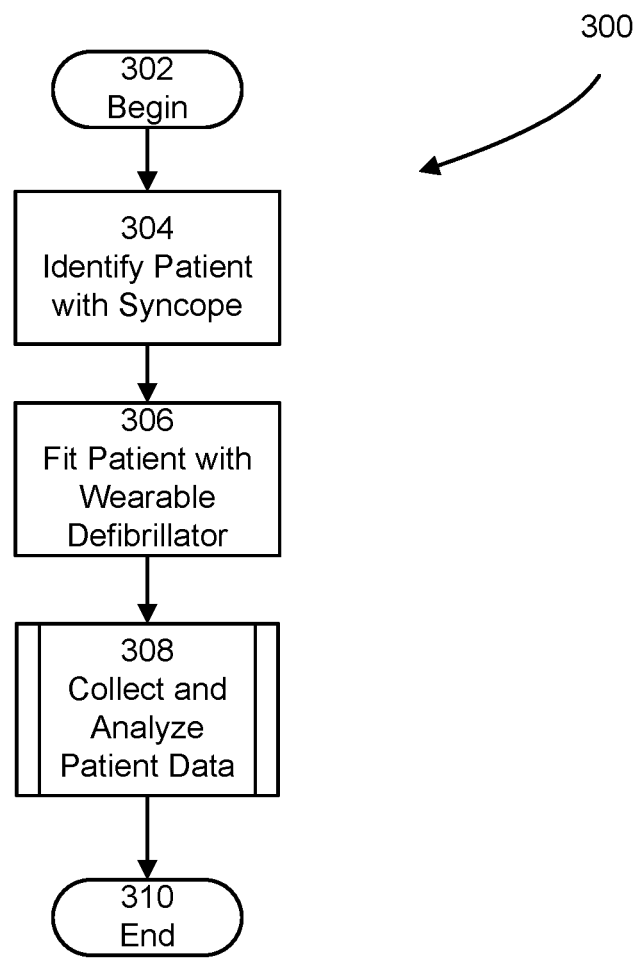
FIG. 3 is a flow diagram of one example of a process for treating a patient with a wearable defibrillator.

In some embodiments, the ECG sensors 202 include ECG Electrodes as described in association with FIG. 3 of the '096 application. Further, in these embodiments, the audio sensors 206 includes a microphone or an accelerometer, and the motion sensors 208 includes an accelerometer. In other embodiments, the treatment electrodes 210 include Therapy Pads as described in association with FIG. 3 of the '096 application. Using these components, the wearable defibrillator 200 may collect, store and analyze data descriptive of a wide variety of physical phenomena such as body impedance (from the ECG sensors 202 or EEG sensors 204), heart sounds and respiratory function (from the audio sensors 206), and patient activity (from the motion sensors 208).

The data collected by the wearable defibrillator 200 may be used to analyze the patient's physiology and behavior. Measurements of body impedance may be used to determine if a patient is sweating. Processing of audio signals may be used to determine if the patient is coughing or if the patient has suffered a pulmonary embolism. Processing of motion data may be used to determine if there has been a change in the patient's gait or an increase in swaying while walking.

For instance, from an accelerometer signal received from the motion sensors 208, the wearable medical device controller 100 may calculate velocity by integrating the acceleration signal. In some embodiments, the motion sensors 208 include multiple accelerometers, or other types of motion sensors such as magnetic based velocity sensing or solid state gyroscopes. These motion sensors 208 may be positioned on various locations of the patient's body such as the shoulder, waist and arms, as the motion of the patient's body will likely vary at each location on the body. Further, the motion sensors 208 may communicate wirelessly with the wearable medical device controller 100 so that the motion sensors 208 can be worn as patches on these various locations. Using the motion sensors 208, the wearable medical device controller 100 can determine the patient's body position and orientation, for instance, whether the patient is standing, sitting, walking or lying down in a prone, supine or on her side.

In some embodiments, the wearable medical device controller 100 is configured to predict impending syncope (i.e., identify a precursor of syncope) by detecting a level of dyskinesia in the patient's motion and comparing the detected level to a baseline dyskinesia for the patient. Where a predefined relationship between the detected dyskinesia and the baseline dyskinesia exists (e.g., detected dyskinesia exceeds baseline dyskinesia by a threshold value), the wearable medical device controller 100 identifies the detected dyskinesia as a precursor event and proceeds accordingly.

For example, in one embodiment configured to identify a precursor of syncope by estimating a level of dyskinesia in a patient's motion, the wearable medical device controller 100 can, based on the patient's body orientation, compare the relative motions of the motion sensors 208 to determine that a patient is swaying in a way that resembles an increased sense of imbalance. For instance, the wearable medical device controller 100 may use motion sensors 208 positioned at the top, middle and lower regions of the patient's torso to estimate swaying of the spine that is also a sign of imbalance. Examples of relative motions of the motion sensors 208 that may be indicative of swaying include increased circular motions that are out of phase between the shoulders and hips, or of increased shaking of higher frequency components in the motion in the region of the knees or ankles, which are areas of balance compensation.

In another embodiment configured to identify a precursor of syncope by estimating a level of dyskinesia in a patient's motion, the wearable medical device controller 100 categorizes gestural motions to characterize the patient behavior, for instance as bending over from a standing position or sitting. In this embodiment, the motion sensors 208 may be worn on the wrist or wrists to determine hand location relative to other portions of the patient's body. For instance, if the patient bends over to pick something up, the wearable medical device controller 100 may, based on gestural motion and relative hand location, categorize the motion as "picking something up." If, however, the patient bends over, but the relative hand location is onto the patient's knee (as indicated by a wrist sensor or other motion sensor 208 disposed in a location to detect arm position), then the wearable medical device controller 100 may categorize the motion as one associated with increased imbalance and dizziness and as a sign of possible impending syncope.

Wearable optical sensors 212 may also be included to enable the wearable medical device controller 100 to create a three dimensional representation of the environment of the patient. For example, in one embodiment the wearable medical device controller 100 controls relative focusing of stereoscopic cameras included within the optical sensors 212. In this embodiment, the wearable medical device controller 100 processes the images provided by the stereoscopic cameras to detect and define various objects in the field of view. The wearable medical device controller 100 may further calculate the distance between the patient and the various objects to create a representation of the space in which the patient is situated (e.g., on the floor, leaning against a wall, etc.).

Exemplary Event Processes

Various embodiments implement and enable processes through which a wearable defibrillator, such as the wearable defibrillator 200, protects a patient from treatable cardiac disorders while monitoring and detecting for causes of other symptoms, such as syncope. FIG. 3 illustrates one such process 300 that includes acts of identifying a patient with syncope, fitting a patient with a wearable defibrillator, and collecting and analyzing patient data. The process 300 begins at 302.

In act 304, a health care professional, such as a physician, evaluates a patient who presents with symptoms indicative of syncope. For instance, according to one example, a patient presents at a hospital emergency department with syncope.

More specifically, in some examples, the health care professional may diagnose a patient as having experienced cardiac syncope or undiagnosed syncope (e.g., a syncopal event with an unknown source, which may or may not be cardiac). In these examples, patients are diagnosed based on one or more of the following criteria: a history, or family history, of cardiovascular disease (e.g. coronary artery disease, heart failure, structural heart disease); abnormal ECG findings (e.g. ischemia, dysrhythmias, conduction abnormalities); advanced age; and low hematocrit count. Based on these, or other, criteria the health care professional identifies a syncopal event within the patient's history.

In act 306, the patient is fitted with a wearable defibrillator, such as the wearable defibrillator 200 described above with reference to FIG. 2, in response to identification of the syncopal event. For instance, continuing the previous example, the patient of the emergency department is outfitted with the wearable defibrillator and sent home for monitoring. In an alternative example, the patient remains in the hospital for observation.

In some embodiments, components of the wearable defibrillator are housed within a garment. In these embodiments, the act 306 includes adjusting the garment to promote contact between the surface of the patient's skin and the electrodes included with the wearable defibrillator. In other embodiments, the wearable defibrillator includes adhesive electrodes. In these embodiments, the act 306 includes applying the adhesive electrodes to the surface of the patient's skin. It is to be appreciated that embodiments including adhesive electrodes may alter or reduce the skill required to fit the patient and may translate well to the pre-existing skill set of particular personnel, such as emergency department personnel.

In act 308, the wearable defibrillator 200 collects and analyzes patient data. Actions performed by the wearable defibrillator 200 during execution of the act 308 are described further below with reference to FIG. 4.

Process 300 ends at 310. Embodiments in accord with process 300 assist a medical professional in diagnosing syncope and identifying its root cause or causes while continuously monitoring the patient and automatically treating cardiac arrhythmias that may occur.

It is to be appreciated that the method 300 may include acts of expressly excluding (e.g. not fitting with a wearable defibrillator) a patient presenting with syncope who has been definitively diagnosed as having experienced non-cardiac syncope, including but not limited to patients having suffered one of the following: vasovagal syncope, orthostatic syncope, carotid sinus syncope, drug-related syncope, and seizure.

Further, it is to be appreciated that the data collected by the wearable defibrillator 200 may allow a medical professional to eliminate potential root causes for syncope in a given patient. For instance, while it is often the case that syncope is caused by disorders involving the cardiovascular system, some patients experience syncopal episodes that are caused by a disorder outside of the cardiovascular system. In these situations, the wearable defibrillator 200 may not be able to prevent a syncopal episode or treat its underlying cause, but by recording physiological data before, during, and after a patient experiences the syncopal episode, the wearable defibrillator 200 may provide the medical professional with information that indicates the root cause of the syncope is not within the cardiovascular system (e.g., information that indicates normal cardiac function before, during, and after the syncopal episode).

Figure 4:
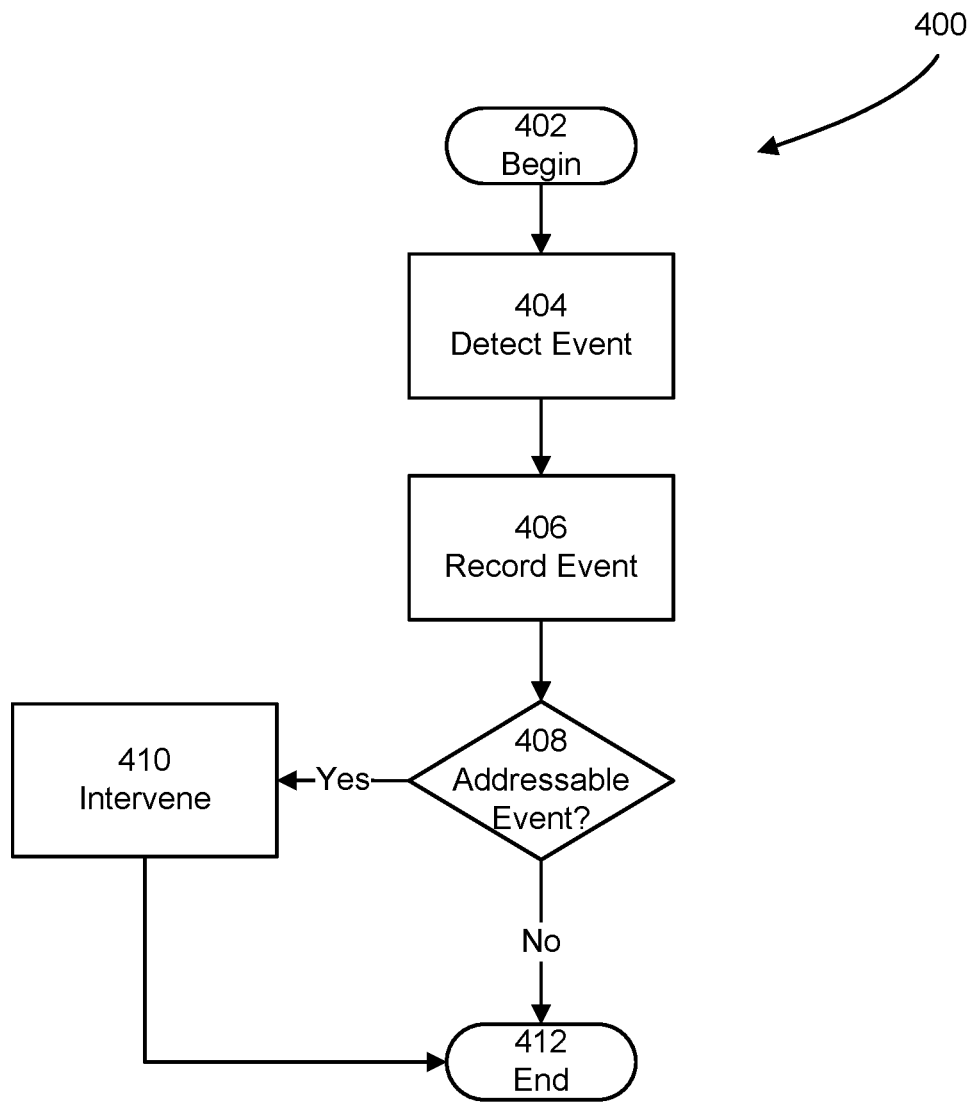
FIG. 4 is a flow diagram of one example of a process of monitoring and treating syncopal events.

As discussed above with regard to act 308 illustrated in FIG. 3, various embodiments implement processes for collecting and analyzing patient data while protecting the patient from one or more treatable cardiac disorders. FIG. 4 illustrates one such process 400 that implements act 308 and that includes acts of detecting an event, recording the event, determining if the event is addressable and addressing the event. In one embodiment, a wearable defibrillator executes the process 400 beginning at 402.

In act 404, an event manager, such as the event manager 114 described above with reference to FIG. 1, detects an event. In some embodiments, when executing the act 404, the event manager first determines which events are active under the currently selected disorder mode. Next, the event manager scans inbound data and identifies any patterns in the data that match a predetermined pattern specified in an active event profile. Events that may be detected by execution of the act 404 include any of the events described herein, such as cardiac arrhythmias, syncope precursors, and user-initiated events.

In act 406, the event manager records the event by storing information descriptive of the event in data storage. This event information may include information descriptive of the type of event, the timing of the event, ECG (or other) signals associated with the event, notifications and responses associated with the event, treatment protocols initiated as a result of the event, the amount of energy delivered during the treatment protocols and the amount of transthoracic impedance encountered measured during the event. In act 408, the event manager determines whether the event is addressable by determining whether the event profile corresponding to the event includes an association with processing logic to be executed after detection of the event. If the event is addressable, the event manager intervenes by executing the processing logic associated with the event in act 410. The intervening actions taken by the wearable defibrillator may include any of the intervening actions described herein, such as pacing a patient's heart, issuing a defibrillation shock, or issuing a notification to an external entity. If the event is not addressable, the event manager proceeds to act 412. In the act 412, the event manager terminates the process 400.

It is to be appreciated that, in some instances, addressing an event by issuing a notification to a patient may have a therapeutic effect (i.e., the notification itself may be a therapeutic treatment). For example, where onset of a syncopal episode is imminent, the issuance of an alarm may cause a physiological response in the patient, such as an adrenaline surge, that averts the syncopal episode.

Examples in accord with process 400 enable a wearable defibrillator to gather, record, and report patient information for use in diagnosing disorders that have many potential causes and that manifest many potential symptoms, such as syncope. By wearing a device over an indefinite period of time, and allowing the patient to return to normal activities, data can be acquired about the patient that can lead to a definitive diagnosis. In addition, because the information is gathered by a wearable defibrillator, the patient is protected against possibly life-threatening cardiac arrhythmias.

Each of the processes disclosed herein depicts one particular sequence of acts in a particular example. The acts included in each of these processes may be performed by, or using, a wearable defibrillator specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a wearable defibrillator configured according to the examples disclosed herein.

Having thus described several aspects of at least one embodiment, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. An external wearable defibrillator for monitoring a patient for cardiac-related events comprising:
   a plurality of ECG sensors configured to be disposed about a torso of the patient;
   a plurality of therapy electrodes configured to be disposed on a first location and a second location on the patient;
   at least one motion sensor;
   wherein the plurality of ECG sensors, the plurality of therapy electrodes, and the at least one motion sensor are configured to be worn continuously by the patient for an extended period of time;
   a wearable medical device controller comprising at least one processor configured to
      receive ECG data from the plurality of ECG sensors;
      receive motion data from the at least one motion sensor,
      using the ECG data received from the plurality of ECG sensors, identify at least one of ventricular tachycardia or ventricular fibrillation,
      initiate a treatment protocol comprising a defibrillation shock after identifying at least one of ventricular tachycardia or ventricular fibrillation,
      using at least one of the ECG data received from the plurality of ECG sensors or the motion data received from the at least one motion sensor, identify a predetermined pattern for a precursor of syncope, wherein the predetermined pattern for the precursor of syncope comprises bradycardia,
      record the predetermined pattern for the precursor of syncope in a memory, and
      perform an intervening action to address the predetermined pattern for the precursor of syncope.

2. The external wearable defibrillator of claim 1, wherein the intervening action comprises issuing a notification to at least one of the patient or a bystander.

3. The external wearable defibrillator of claim 2, wherein the notification to the at least one of the patient or the bystander comprises at least one of a prompt for the patient to sit down or a prompt to call for help.

4. The external wearable defibrillator of claim 1, wherein the intervening action comprises issuing a notification to at least one of a caregiver or a medical professional.

5. The external wearable defibrillator of claim 1, wherein the intervening action comprises pacing a heart of the patient via the plurality of therapy electrodes.

6. The external wearable defibrillator of claim 1, further comprising a syncope response button configured to be pressed by the patient to record a syncopal event.

7. The external wearable defibrillator of claim 6, wherein the at least one processor is further configured to record the syncopal event in the memory in response to the patient pressing the syncope response button.

8. The external wearable defibrillator of claim 1, wherein the at least one processor is further configured to identify the precursor of syncope by determining relative motions of the patient using the motion data from the at least one motion sensor.

9. The external wearable defibrillator of claim 8, wherein the at least one processor is further configured to identify the precursor of syncope by estimating a level of dyskinesia in the patient's motion based on the determined relative motions of the patient.

10. The external wearable defibrillator of claim 9, wherein the at least one processor is further configured to identify the precursor of syncope by comparing the estimated level of dyskinesia in the patient's motion to a baseline dyskinesia for the patient.

11. The external wearable defibrillator of claim 1, wherein the wearable medical device controller comprises the memory.

12. The external wearable defibrillator of claim 1, wherein the wearable medical device controller further comprises a network interface.

13. The external wearable defibrillator of claim 12, wherein the at least one processor is configured to transmit the predetermined pattern for the precursor of syncope to a remote server via the network interface.

14. The external wearable defibrillator of claim 1, further comprising a wearable garment configured to house the plurality of ECG sensors, the plurality of therapy electrodes, and the at least one motion sensor.

15. The external wearable defibrillator of claim 1, wherein at least one of the plurality of ECG sensors and/or the plurality of therapy electrodes is configured to be adhesively applied to a surface of the patient's skin.

16. The external wearable defibrillator of claim 1, wherein the at least one processor is further configured to initiate a responsiveness test in response to identifying the at least one of ventricular tachycardia or ventricular fibrillation.

17. The external wearable defibrillator of claim 16, wherein the responsiveness test comprises issuing a notification indicating that a therapeutic shock is imminent.

18. The external wearable defibrillator of claim 17, wherein the notification indicating that the therapeutic shock is imminent comprises an audible tone that escalates in volume.

19. The external wearable defibrillator of claim 17, further comprising one or more target response buttons, wherein the responsiveness test further comprises waiting for an actuation of the one or more target response buttons.

20. The external wearable defibrillator of claim 19, wherein the at least one processor is configured to initiate the treatment protocol comprising the defibrillation shock after identifying the at least one of ventricular tachycardia or ventricular fibrillation and after no actuation of the one or more target response buttons.

\* \* \* \* \*